(12) United States Patent
Shelton

(10) Patent No.: US 6,521,871 B1
(45) Date of Patent: Feb. 18, 2003

(54) THERMALIZING APPARATUS

(75) Inventor: Winston Shelton, Louisville, KY (US)

(73) Assignee: Carton Drive Enterprises LLC, Louisville, KY (US)

( * ) Notice: Subject to any disclaimer, the term of this patent is extended or adjusted under 35 U.S.C. 154(b) by 0 days.

(21) Appl. No.: 09/953,774

(22) Filed: Sep. 17, 2001

(51) Int. Cl.[7] .............. A21B 1/24; A21B 3/04; G01N 25/64; F27D 7/02
(52) U.S. Cl. ............ 219/401; 219/413; 126/20
(58) Field of Search ............... 219/396, 398, 219/401, 413; 99/468; 126/20, 20.1, 20.2

(56) References Cited

U.S. PATENT DOCUMENTS

| | | | | |
|---|---|---|---|---|
| 4,048,473 A | * | 9/1977 | Burkhart | 219/413 |
| 4,623,780 A | * | 11/1986 | Shelton | 219/401 |
| 4,674,402 A | * | 6/1987 | Raufeisen | 219/401 |
| 4,722,268 A | | 2/1988 | Rightley | |
| 4,770,888 A | * | 9/1988 | Loeb | 426/520 |
| 5,075,120 A | * | 12/1991 | Leary et al. | 426/233 |
| 5,494,690 A | | 2/1996 | Shelton | |
| 5,558,010 A | | 9/1996 | Shelton | |
| 5,595,109 A | | 1/1997 | Shelton | |
| 5,836,086 A | * | 11/1998 | Elder | 34/396 |
| 5,934,178 A | * | 8/1999 | Caridis et al. | 219/401 |

FOREIGN PATENT DOCUMENTS

| | | | |
|---|---|---|---|
| JP | 7-87932 | * | 9/1988 |
| JP | 63294856 | * | 12/1988 |
| JP | 63-214655 | * | 4/1995 |

* cited by examiner

Primary Examiner—Joseph Pelham
(74) Attorney, Agent, or Firm—Theresa Fritz Camoriano

(57) ABSTRACT

A food thermalizer includes a food chamber which is vented to atmosphere. A wet bulb temperature sensor preferably is located adjacent to the vent and uses the condensate in the vent to keep its outer surface wet. By sensing the wet bulb temperature within the food chamber and controlling a wet heat source that heats the water in an evaporator in the food chamber, the vapor surrounding the food can serve as a vapor thermostat to control the final food temperature. The cook also can control the dry bulb temperature relative to the wet bulb temperature by controlling a dry heat source that heats the air, thereby controlling the degree of browning or texturing of the food.

8 Claims, 2 Drawing Sheets

THERMALIZING APPARATUS

BACKGROUND OF THE INVENTION

The present invention relates to an apparatus and a method for thermalizing (raising of dough, hot food holding, poaching, roasting, baking, steaming, or otherwise heating or maintaining the temperature of food) in an oven, and more specifically, thermalizing the food in a manner which accurately and predictably controls the doneness temperature of the food item as well as the degree of browning or texturing of the food item.

Traditional ovens characteristically utilize a dry heat system. The limitations of this equipment have led users to develop alternate cooking techniques, such as papillote cooking (bag cooking) in an effort to have some control over the parameters which actually affect the quality of the end product. Winston Industries has manufactured ovens or thermalizers having water reservoirs (evaporators), in which the temperature of water in the evaporator was controlled, and these ovens or thermalizers have provided a much improved ability to control the quality of the food.

However, it has been found that controlling the temperature of the water in the evaporator is not enough to provide the most accurate control of the temperature and moisture of the food itself. Since the oven or thermalizer is vented, the conditions inside the food chamber are not the same as the conditions at the evaporator.

SUMMARY OF THE INVENTION

The present invention provides a wet bulb temperature sensor inside the food chamber, which much more closely represents the condition of the food being prepared. This wet bulb sensor preferably is located near the oven vent and preferably is kept wet by the condensate of the vapor leaving the food chamber through the vent, and thus senses the same conditions that the food is being subjected to.

In a preferred embodiment, a temperature sensor projects into the vent, which has a perforated funnel shape, and a wire spring that is wrapped around the bottom portion of the temperature sensor catches the condensate in the funnel-shaped vent area and, through capillary action, created by the small gap between the wire and the bulb, this condensate coats the surface of the bottom portion of the temperature sensor, making it a wet bulb temperature sensor.

The control system then controls the wet bulb temperature inside the food chamber by controlling a heater inside the evaporator (a wet heater), and it controls the difference between the dry bulb temperature and the wet bulb temperature by controlling a heater that heats the air in the food chamber (a dry heater).

The food itself is like a wet bulb sensor, since it has a moist outer surface and is sensing the conditions inside the oven, so the wet bulb sensor closely approximates the conditions of the food. By being able to control the wet bulb temperature and the difference between the wet bulb temperature and the dry bulb temperature inside the food chamber, the cook can control the temperature and the browning or texturing of the food.

Thus, this thermalizer or oven gives the cook a superior ability to control the quality of food and to reproduce that quality on a regular basis.

DESCRIPTION OF THE PREFERRED EMBODIMENT

Figure 1:
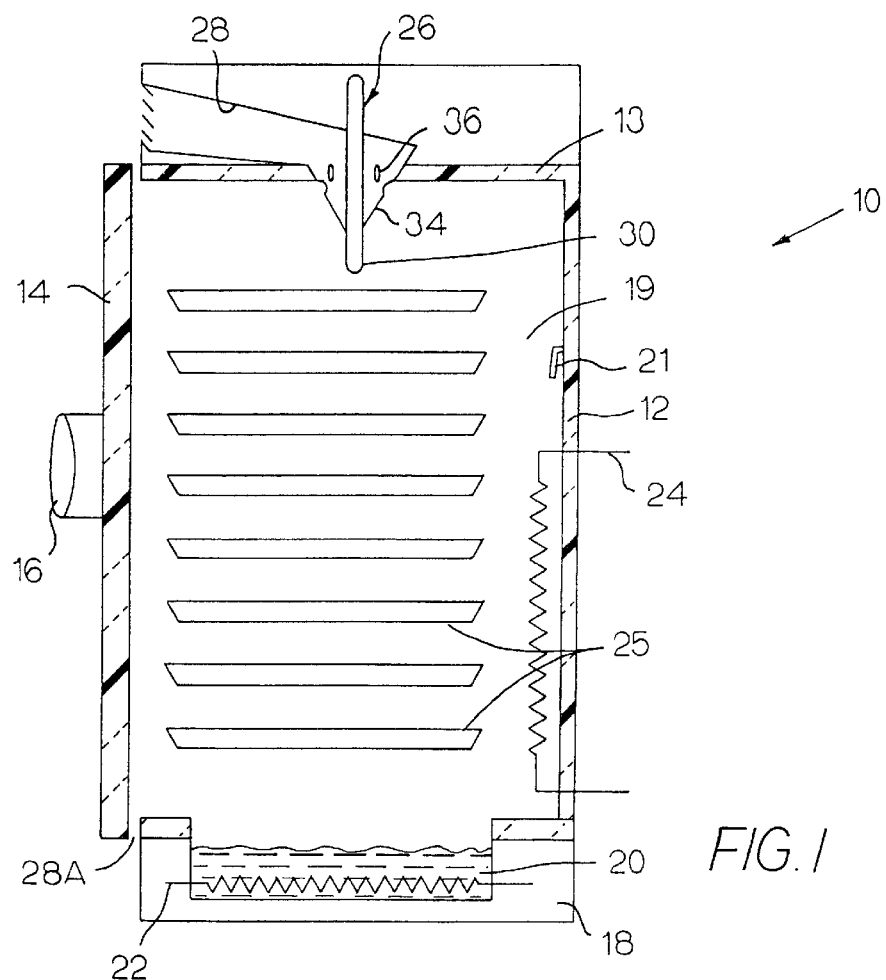
FIG. 1 is a schematic side sectional view of a thermalizer or oven made in accordance with the present invention.
Figure 2:
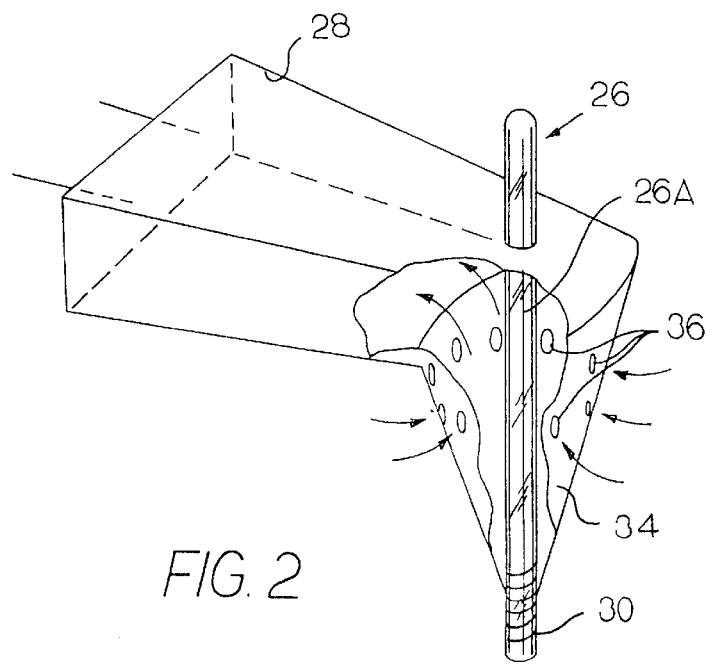
FIG. 2 is a broken away, perspective detail view of the wet bulb thermostat of the oven of FIG. 1; and, FIG. 3 is a schematic diagram of the control system for the thermalizer of the present invention.

FIG. 1 shows an example of a thermalizer or oven 10 made in accordance with the present invention. The thermalizer or oven 10 includes a substantially closed food chamber, having a back wall 12, a top wall 13, a front wall 14 (which is actually a door 14 with a handle 16), a bottom wall 18, and two side walls 19. The bottom wall 18 includes a evaporator 20, which holds water. An electrical resistance heater 22 (which provides a wet heat source) is submerged in the water in the evaporator 20. All the walls of the thermalizer 10 are insulated with the exception of the sides and bottom of the evaporator 20. Another electric resistance heater 24 is located along the back wall 12 of the food chamber and serves as a dry heat source as will be described in more detail later. A plurality of trays or racks 25, located inside the thermalizer 10, are supported by the side walls 19 and may be used for holding food items (not shown).

The top wall 13 of the oven or thermalizer 10 defines a vent duct 28, which provides an opening from the interior of the food chamber to the air surrounding the oven 10. There is a gasket around the top and sides of the oven door 14, but there is no gasket at the bottom of the door 14, creating an inlet vent duct 28A at the bottom of the oven to allow entry of ambient atmosphere. At the bottom of the vent duct 28 is a funnel-shaped, uninsulated portion 34, defining a plurality of holes 36. The funnel-shaped portion has walls tapering downwardly toward the food chamber. In order for vapor to leave the food chamber and pass to the surrounding atmosphere, the vapor passes through the holes 36 and out the vent duct 28. A cylindrical tube 26 houses a temperature sensor 26A and projects from inside the food chamber axially through the funnel-shaped portion 34 of the vent duct 28. A wire spring 30, having a circular cross-section, is wrapped around the bottom portion of the tube 26 from inside the funnel-shaped portion of the duct to inside the food chamber. The spring 30 has a spiral line contact with the tube 26 and lies closely adjacent to the inner wall of the funnel-shaped portion 34 of the duct 28. Some of the vapor traveling along the uninsulated vent duct 28 condenses along the vent duct walls, and the condensate trickles back along the downwardly-sloping duct wall, into the funnel-shaped portion 34, passing downwardly along the tapered walls of the funnel-shaped portion, to the spring 30. Through a capillary action, caused by the small gaps between the spring 30 and the wall of the tube 26 adjacent to the spiral line of contact, the condensate is wicked along the surface of the lower portion of the tube 26, keeping the lower portion of the tube 26 wet, so that it functions as a wet bulb that is sensed by temperature sensor 26A.

While it is preferred to use the metal spring 30 to provide the wicking to spread the condensate over the surface of the bulb in order to keep it wet, a variety of known mechanisms could be used to transport the condensate from the vent 28 to the tube 26 in order to keep it wet. For example, other types of wicking could be used, a tube could transport the condensate to the sensor area of the tube by gravity, and so forth. It would also be possible to pump the condensate water or to provide water from another source to thinly coat the surface of the tube 26, so it functions as a wet bulb whose temperature is sensed by sensor 26A.

There is also a dry bulb temperature sensor 21 in the food chamber to sense the dry bulb temperate inside the food chamber.

Figure 3:
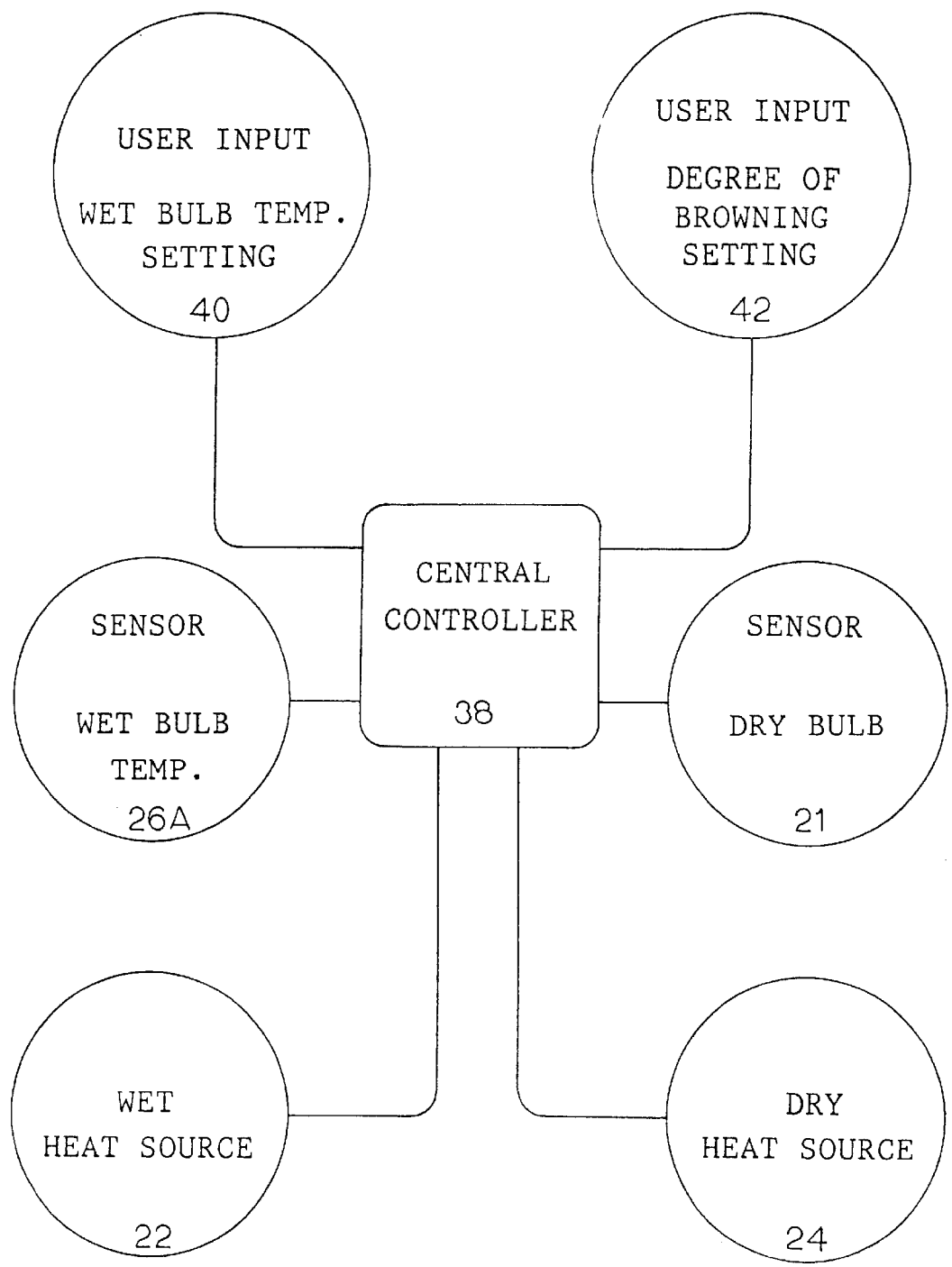

As shown in FIG. 3, the dry bulb temperature and the wet bulb temperature from the sensors 21 and 26A, respectively, are transmitted to a central controller 38, which controls the power to the two resistance heaters 22, 24 based on settings the cook has set on the thermalizer controls.

The thermalizer 10 includes a first user input 40 that allows the cook to set the desired wet bulb temperature and a second user input 42 that allows the cook to select a value (0–10) representing degrees of browning or texturing (0 meaning no browning or texturing; 10 meaning high browning or texturing). The first input 40 corresponds to food temperature. The second input 42 corresponds to increasing differences between the wet bulb and dry bulb temperature in the food chamber, as indicated by the following table:

Browning or Texturing Scale:

| Selected value | 0 | 1 | 2 | 3 | 4 | 5 | 6 | 7 | 8 | 9 | 10 |
|---|---|---|---|---|---|---|---|---|---|---|---|
| Difference in degrees Fahrenheit between wet bulb temp and dry bulb temp. | 0 | 5 | 10 | 20 | 30 | 40 | 50 | 75 | 100 | 125 | 150 |

Operation of the Thermalizer

The cook inserts the food into the oven 10, sets the wet bulb temperature input 40 and sets the degree of browning or texturing by inputting the desired value on the browning or texturing scale 42. These inputs may be by buttons, dials, or other known input means. The controller 38 then controls the power to the wet heat source 22 and the dry heat source 24, to control the wet bulb temperature measured by the sensor 26A and the dry bulb temperature measured by the sensor 21 according to those inputs.

If the food is colder than the wet bulb temperature in the thermalizer 10, the vapor in the thermalizer 10 condenses on the food surface, transferring its latent heat of vaporization to the food to raise the temperature of the foods, and it continues to do so until the food reaches the wet bulb temperature sensed by the wet bulb sensor 26A. If the food is warmer than the wet bulb temperature in the thermalizer 10, the food releases moisture to the thermalizer 10, thus lowering the food temperature through loss of heat through vaporization. It continues to do so until, once again, the food reaches the wet bulb temperature of the thermalizer 10.

As the temperature of food is being increased as in cooking, the food will begin at a temperature that is less than the wet bulb temperature in the thermalizer, since the food generally has a large mass and does not heat as quickly as the wet bulb temperature sensor, and it will approach the wet bulb temperature of the sensor 26A as the cooking time progresses.

The thermalizer 10 includes an evaporator 20 with a heat source 22 (referred hereinafter as a wet heat source) to regulate the water temperature. The thermalizer also includes a dry heat source 24. While the evaporator 20 is shown here as being in the food chamber, it may be in a separate chamber that is in communication with the food chamber through vents, as is known in the prior art. The central controller will apply power to the wet heat source 22 as needed to maintain the pre-set wet bulb temperature at the wet bulb sensor 26A. The central controller 38 will also apply power to the dry heat source 24 as needed to maintain the pre-set temperature differential between the wet bulb temperature at the wet bulb sensor 26A and the dry bulb temperature at the dry bulb sensor 21.

Once the water temperature has been set, for example at 135 degrees F, a partial pressure of water vapor is established in the thermalizer 10. The wet heat source 22 continues to evaporate water from the evaporator 20 until a partial pressure equilibrium is reached in the thermalizer 10 corresponding to the partial pressure of water at 135 degrees F. If the food temperature is below 135 degrees F, the food acts as a condenser, condensing some of the vapor in the thermalizer 10, which heats the food (as the vapor gives up its latent heat of vaporization to the food) and which lowers the partial pressure of the vapor in the thermalizer 10. The lower partial pressure of vapor in the thermalizer 10 reduces the wet bulb temperature of the wet bulb sensor 26A, which causes the controller 38 to turn on the wet heat source 22, causing more water to evaporate from the evaporator 20 in order to maintain the equilibrium pressure corresponding to the set wet bulb temperature of 135 degrees F. As water evaporates from the evaporator 20, it cools the evaporator 20, so the wet heat source 22 must also heat the evaporator 20 to overcome the effects of this evaporative cooling. This process continues until the food has reached equilibrium at the set point temperature of 135 degrees F.

At the same time, the central controller 38 will cause the dry heat source 24 to cycle on and off to maintain the pre-set difference in temperature between the dry bulb and the wet bulb temperatures based on the user input 42 for the degree of browning or texturing.

In the event that preheated food is introduced to the thermalizer 10 at a temperature higher than the preset wet bulb temperature (of say 135 degrees F), the same phenomenon takes place as before, except that the food becomes the heat source and the evaporator 20 becomes a heat sink. The food releases its heat by generating vapor, which increases the partial pressure of the vapor in the thermalizer 10 to a value higher than the partial pressure of the vapor from the evaporator and condensation of vapor from the foods will take place upon the evaporator. The central controller will sense an increase in wet bulb temperature at the sensor 26A and thus will turn off power to the wet heat source 22, as it tries to control the wet bulb temperature of the sensor 26A at the pre-set wet bulb temperature. This process continues until the food has reached equilibrium at the set point temperature of 135 degrees F.

The difference between the dry bulb temperature and wet bulb temperature is the driving force to evaporate moisture from the food; the higher the difference, the higher the evaporation rate from the food. This greater difference results in a higher degree of browning or texturing of the food item.

As the moisture leaves the surface of the food items, chemical components are concentrated on the surface and this, together with the high temperatures, causes the browning or texturing of the food item. With the thermalizer 10 vented properly, the wet heat source 22 is cycled on and off as needed to control the wet bulb temperature sensed by the wet bulb sensor 26A, thus controlling the food temperature. The dry heat source 24 is cycled on and off as needed to control the temperature difference between the dry bulb temperature sensed by the sensor 21 (which is simply the air temperature in the thermalizer 10) and the wet bulb temperature sensed by the sensor 26A.

Thus, in the present invention, a cook sets a desired food temperature by setting the desired wet bulb temperature on the input 40. The user also sets the desired degree of browning or texturing on the browning or texturing control 42 indicating a browning or texturing scale of 0 to 10, where 0 is no browning or texturing at all and 10 is the highest level of browning or texturing. The central controller 38 takes the browning or texturing setting and controls the dry heat source 24 to maintain a difference between the dry-bulb temperature at the dry bulb sensor 21 and the wet bulb temperature at the wet bulb sensor 26A corresponding to the degree of browning or texturing selected by the cook, in accordance with the aforementioned table. The result is a properly thermalized food item to the desired level of doneness (food temperature) and to the desired texture (degree of browning or texturing) on a consistent basis and without frequent inspections by the cook.

While the preferred embodiment described above uses electrical resistance heaters, other types of heaters are also known in the art and could be used, such as gas. In that case, the controller 38 would be controlling the gas flame rather than controlling the electrical power. Also, there would be some type of heat exchanger between the gas heat source and the water in the evaporator, since air must get to the gas in order for it to burn. It will be obvious to those skilled in the art that these and many other modifications may be made to the embodiment described above without departing from the scope of the invention as claimed.

What is claimed is:

1. A thermalizer for cooking food, comprising:

a food chamber;

an evaporator in communication with said food chamber, including a first heat source which heats the water in the evaporator;

a second heat source which heats the air inside the food chamber;

a vent providing a path from inside of said food chamber to outside of said food chamber, for venting vapor;

a wet bulb temperature sensor in said food chamber, wherein said wet bulb sensor is kept wet by condensate from said vent;

a dry bulb temperature sensor in said food chamber; and a controller which controls said first and second heat sources based on signals received from said wet bulb temperature sensor and said dry bulb temperature sensor.

2. A thermalizer as recited in claim 1, wherein said wet bulb sensor is located adjacent to said vent.

3. A thermalizer for cooking food, comprising:

a food chamber;

an evaporator in communication with said food chamber, including a first heat source which heats the water in the evaporator;

a second heat source which heats the air inside the food chamber;

a vent providing a path from inside of said food chamber to outside of said food chamber, for venting vapor, wherein said vent includes an upwardly sloping duct;

a wet bulb temperature sensor in said food chamber, wherein said wet bulb temperature sensor lies adjacent to said upwardly sloping duct to receive condensate from said duct;

a dry bulb temperature sensor in said food chamber;

a controller which controls said first and second heat sources based on signals received from said wet bulb temperature sensor and said dry bulb temperature sensor; and further comprising a coil wrapped around at least a portion of said wet bulb temperature sensor for wicking condensate from said duct to said wet bulb temperature sensor.

4. A thermalizer as recited in claim 3, wherein said vent includes a funnel-shaped portion, and said wet bulb temperature sensor is located axially in said funnel-shaped portion.

5. A thermalizer, comprising:

a food chamber;

an evaporator in fluid communication with said food chamber;

a controller;

a dry heat source controlled by said controller;

a wet heat source controlled by said controller;

a wet bulb temperature sensor located in said food chamber and in communication with said controller;

a dry bulb temperature sensor located in said food chamber and in communication with said controller;

a user input in communication with said controller to set the wet bulb temperature in said food chamber;

a user input in communication with said controller to set the dry bulb temperature, wherein said controller controls the wet heat source and the dry heat source to reach the user input settings, and further comprising a vent from said food chamber to atmosphere, said vent having downwardly-sloping walls;

wherein said wet bulb temperature sensor is located adjacent to said vent so as to receive condensate from said vent.

6. A thermalizer as recited in claim 5, wherein said vent includes a funnel-shaped portion defining a plurality of holes, and wherein said wet bulb temperature sensor extends axially through said funnel-shaped portion and projects into said food chamber, so that condensate from said vent runs down said funnel-shaped portion to wet said wet bulb temperature sensor.

7. A thermalizer as recited in claim 5, and further comprising a wick extending from said vent to said wet bulb temperature sensor.

8. A thermalizer as recited in claim 7, wherein said wick comprises a wire coil wrapped around said wet bulb temperature sensor.

* * * * *